United States Patent [19]
Savoca et al.

[11] Patent Number: 5,756,558
[45] Date of Patent: May 26, 1998

[54] HYDROXYALKYLBIS(AMINOETHYL) ETHER COMPOSITIONS FOR THE PRODUCTION OF POLYURETHANES

[75] Inventors: Ann Coates Lescher Savoca, Bernville; Richard Paul Underwood; Richard Van Court Carr, both of Allentown; James Stephen Emerick, Whitehall, all of Pa.

[73] Assignee: Air Products and Chemicals, Inc., Allentown, Pa.

[21] Appl. No.: 675,127

[22] Filed: Jul. 3, 1996

[51] Int. Cl.$^6$ .................................................. C08G 18/18
[52] U.S. Cl. ...................... 521/167; 528/49; 528/53; 528/85; 521/115; 564/471; 564/473; 564/507; 564/508
[58] Field of Search .................... 528/49, 53, 85; 521/167, 115; 564/471, 473, 508, 507

[56] References Cited

U.S. PATENT DOCUMENTS

| | | | |
|---|---|---|---|
| 4,210,605 | 7/1980 | Hoshino | 252/476 |
| 4,338,408 | 7/1982 | Zimmerman et al. | 521/115 |
| 4,433,170 | 2/1984 | Zimmerman et al. | 564/508 |

FOREIGN PATENT DOCUMENTS

| | | |
|---|---|---|
| 59134754 | 8/1984 | Japan. |

OTHER PUBLICATIONS

N. Malwitz, et al. "Amine Catalysts of Polyurethane Foam", *Journal of Cellular Plastics*, 23, pp. 461-502, 1987.

*Primary Examiner*—Rachel Gorr
*Attorney, Agent, or Firm*—Michael Leach

[57] ABSTRACT

A method for preparing a polyurethane foam which comprises reacting an organic polyisocyanate and a polyol in the presence of a blowing agent, a cell stabilizer and a catalyst composition comprising a compound having the following formula I:

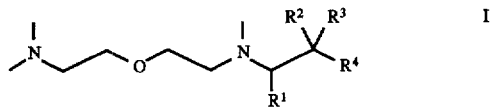

where

- $R^1$ is hydrogen or a linear or branched C1–C4 alkyl or a C1–C4 hydroxyalkyl group;
- $R^2$ and $R^3$ independently are hydrogen, hydroxy, a linear or branched C1–C4 alkyl or a linear or branched C1–C4 hydroxyalkyl group; and
- $R^4$ is a linear or branched C1–C10 hydroxyalkyl group.

2 Claims, No Drawings

HYDROXYALKYLBIS(AMINOETHYL) ETHER COMPOSITIONS FOR THE PRODUCTION OF POLYURETHANES

TECHNICAL FIELD OF THE INVENTION

The present invention relates to the use of hydroxyalkylbis(aminoethyl) ether derivatives as catalysts for producing polyurethanes.

BACKGROUND OF THE INVENTION

Polyurethane foams are widely known and used in automotive, housing and other industries. Such foams are produced by reaction of a polyisocyanate with a polyol in the presence of various additives. One such additive is a chlorofluorocarbon (CFC) blowing agent which vaporizes as a result of the reaction exotherm, causing the polymerizing mass to form a foam. The discovery that CFC's deplete ozone in the stratosphere has resulted in mandates diminishing CFC use. Production of water-blown foams, in which blowing is performed with $CO_2$ generated by the reaction of water with the polyisocyanate, has therefore become increasingly important. Tertiary amine catalysts are typically used to accelerate blowing (reaction of water with isocyanate to generate $CO_2$) and gelling (reaction of polyol with isocyanate).

The ability of the tertiary amine catalyst to selectively promote either blowing or gelling is an important consideration in selecting a catalyst for the production of a particular polyurethane foam. If a catalyst promotes the blowing reaction too selectively, much of the $CO_2$ will be evolved before sufficient reaction of isocyanate with polyol has occurred, and the $CO_2$ will bubble out of the formulation, resulting in collapse of the foam. A foam of poor quality will be produced. In contrast, if a catalyst too strongly promotes the gelling reaction, a substantial portion of the $CO_2$ will be evolved after a significant degree of polymerization has occurred. Again, a poor quality foam, this time characterized by high density, broken or poorly defined cells, or other undesirable features, will be produced.

Tertiary amine catalysts generally are malodorous and offensive and many have high volatility due to low molecular weight. Release of tertiary amines during foam processing may present significant safety and toxicity problems, and release of residual amines from consumer products is generally undesirable.

Amine catalysts which contain active hydrogen functionality (e.g., —OH, —$NH_2$, and —NHR) often have limited volatility and low odor when compared to related structures which lack this functionality. Furthermore, catalysts which contain active hydrogen functionality chemically bond into the urethane during the reaction and are not released from the finished product. Catalyst structures which embody this concept are typically of low to moderate activity and promote both the blowing (water-isocyanate) and the gelling (polyol-isocyanate) reactions to varying extents.

Secondary alcohols are preferred in the structures because these catalysts exhibit a desirable balance between their promotion of the active hydrogen-isocyanate reactions and their own reactivity with isocyanates. In contrast, catalysts which contain primary alcohols react rapidly with isocyanates and thus high use levels are required. Catalysts which contain tertiary alcohols react slowly with isocyanates, but the urethanes of tertiary alcohols which are formed have poor thermal stability. These urethanes may degrade and release the catalyst at temperatures substantially below the decomposition temperature of the foam itself. The free amine could then accelerate foam decomposition.

Catalysts containing active hydrogen functionality of the type —$NH_2$ and —NHR are less well known.

Catalysts which strongly promote the water-isocyanate (blowing) reaction include tertiary amine structures based on the diethylenetriamine skeleton, in particular pentamethyldiethylenetriamine, and the β-(N,N-dimethylamino)alkyl ethers, in particular bis(N,N-dimethylaminoethyl) ether. Low odor, reactive catalysts structurally related to bis(N,N-dimethylaminoethyl) ether are described in U.S. Pat. Nos. 4,338,408 and 4,433,170. Texacat® ZF-10 catalyst, 2-[N-(dimethylaminoethoxyethyl)-N-methylamino]ethanol, is an effective blowing catalyst, albeit less effective than bis(N,N-dimethylaminoethyl) ether.

SUMMARY OF THE INVENTION

The present invention provides a composition for catalyzing the trimerization of an isocyanate and the reaction between an isocyanate and a compound containing a reactive hydrogen, e.g., the blowing reaction and the gelling (urethane) reaction for making polyurethane. The catalyst composition consists essentially of a compound having the following formula I:

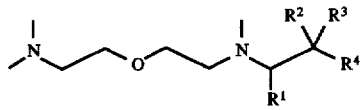

where
- $R^1$ is hydrogen or a C1–C4 linear or branched alkyl or a C1–C4 hydroxyalkyl group;
- $R^2$ and $R^3$ independently are hydrogen, hydroxy, a C1–C4 linear or branched alkyl or a C1–C4 linear or branched hydroxyalkyl group; and
- $R^4$ is a C1–C10 linear or branched hydroxyalkyl group.

It is to be understood in above Formula I that each "—" on a nitrogen atom represents a methyl group, e.g., N— represents N-Me.

The advantage of these catalysts are their combination of low odor and high activity. Additionally, compounds of this type contain functionality which is reactive with isocyanate and will chemically bond into the urethane during the reaction so that the compound is not released from the finished product.

DETAILED DESCRIPTION OF THE INVENTION

The catalyst compositions according to the invention can catalyze (1) the reaction between an isocyanate functionality and an active hydrogen-containing compound, i.e. an alcohol, a polyol, an amine or water, especially the urethane (gelling) reaction of polyol hydroxyls with isocyanate to make polyurethanes and the blowing reaction of water with isocyanate to release carbon dioxide for making foamed polyurethanes, and/or (2) the trimerization of the isocyanate functionality to form polyisocyanurates.

The polyurethane products are prepared using any suitable organic polyisocyanates well known in the art including, for example, hexamethylene diisocyanate, phenylene diisocyanate, toluene diisocyanate ("TDI") and 4,4'-diphenyl-methane diisocyanate ("MDI"). Especially suitable are the 2,4- and 2,6-TDI's individually or together as their commercially available mixtures. Other suitable isocyanates are mixtures of diisocyanates known commercially as "crude MDI", also known as PAPI, which contain about 60% of 4,4'-diphenylmethane diisocyanate along with other isomeric and analogous higher polyisocyanates. Also suitable are "prepolymers" of these polyisocyanates comprising a partially prereacted mixture of a polyisocyanate and a polyether or polyester polyol.

Illustrative of suitable polyols as a component of the polyurethane composition are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols; for example, among others, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane and like low molecular weight polyols.

In the practice of this invention, a single high molecular weight polyether polyol may be used. Also, mixtures of high molecular weight polyether polyols such as mixtures of di- and trifunctional materials and/or different molecular weight or different chemical composition materials may be used.

Useful polyester polyols include those produced by reacting a dicarboxylic acid with an excess of a diol, for example, adipic acid with ethylene glycol or butanediol, or reacting a lactone with an excess of a diol such as caprolactone with propylene glycol.

In addition to the polyether and polyester polyols, the masterbatches, or premix compositions, frequently contain a polymer polyol. Polymer polyols are used in polyurethane foam to increase the foam's resistance to deformation, i.e. to increase the load-bearing properties of the foam. Currently, two different types of polymer polyols are used to achieve load-bearing improvement. The first type, described as a graft polyol, consists of a triol in which vinyl monomers are graft copolymerized. Styrene and acrylonitrile are the usual monomers of choice. The second type, a polyurea modified polyol, is a polyol containing a polyurea dispersion formed by the reaction of a diamine and TDI. Since TDI is used in excess, some of the TDI may react with both the polyol and polyurea. This second type of polymer polyol has a variant called PIPA polyol which is formed by the in-situ polymerization of TDI and alkanolamine in the polyol. Depending on the load-bearing requirements, polymer polyols may comprise 20–80% of the polyol portion of the masterbatch.

Other typical agents found in the polyurethane foam formulations include chain extenders such as ethylene glycol and butanediol; crosslinkers such as diethanolamine, diisopropanolamine, triethanolamine and tripropanolamine; blowing agents such as water, methylene chloride, trichlorofluoromethane, and the like; and cell stabilizers such as silicones.

A general polyurethane flexible foam formulation having a 1–3 lb/ft³ (16–48 kg/m³) density (e.g., automotive seating) containing a gelling catalyst such as triethylenediamine (TEDA) and a blowing catalyst such as a catalyst composition according to the invention would comprise the following components in parts by weight (pbw):

| Flexible Foam Formulation | pbw |
| --- | --- |
| Polyol | 20–100 |
| Polymer Polyol | 80–0 |
| Silicone Surfactant | 1–2.5 |
| Blowing Agent | 2–4.5 |
| Crosslinker | 0.5–2 |

| Flexible Foam Formulation | pbw |
| --- | --- |
| Catalyst | 0.25–2 |
| Isocyanate Index | 70–115 |

The blowing catalyst composition composing part of the catalyst in the above foam formulation is a compound represented by formula I:

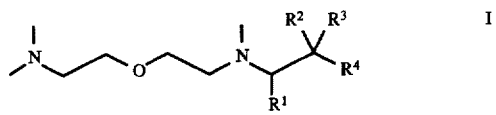

where

R¹ is hydrogen, a C1–C4 linear or branched alkyl or a C1–C4 hydroxyalkyl group;

R² and R³ are independently hydrogen, hydroxy, a C1–C4 linear or branched alkyl or a C1–C4 linear or branched hydroxyalkyl group; and R⁴ is a C1–C10 linear or branched hydroxyalkyl group.

It is preferred that R¹ and R² are hydrogen, R³ is hydrogen or hydroxy, and R⁴ is a C1–C4 linear or branched hydroxyalkyl group.

Alkyl groups would include, for example, methyl, ethyl, propyl and butyl; hydroxyalkyl groups would include, for example, hydroxymethyl, hydroxyethyl, hydroxybutyl, hydroxyethylhexyl, and the like.

Exemplary of suitable catalysts are compounds of the following structures Ia through Id:

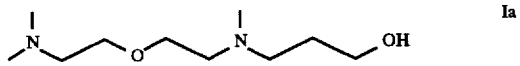

N,N,N'-trimethyl-N'-(3-hydroxypropyl)bis(aminoethyl) ether
[Ia: R¹, R², R³ = H; R⁴ = CH₂OH]

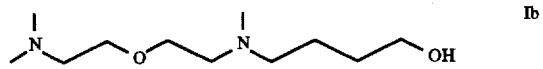

N,N,N'-trimethyl-N'-(4-hydroxybutyl)bis(aminoethyl) ether
[Ib: R¹, R², R³ = H; R⁴ = CH₂CH₂OH]

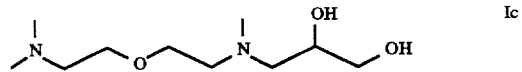

N,N,N'-trimethyl-N'-(2,3-dihydroxypropyl)bis(aminoethyl) ether
[Ic: R¹, R² = H; R³ = OH; R⁴ = CH₂OH]

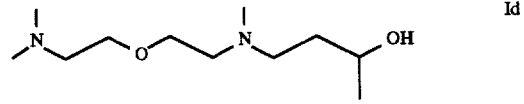

N,N,N'-trimethyl-N'-(3-hydroxybutyl)bis(aminoethyl) ether
[Id: R¹, R², R³ = H; R⁴ = CH(OH)CH₃]

The preferred catalyst composition is N,N,N'-trimethyl-N'-(4-hydroxybutyl)bis(aminoethyl) ether [Ib].

The preferred route to catalyst compositions of this type would be a three step process involving the reductive amination of bisaminoethyl ether II with less than stoichiometric amounts of a carbonyl compound of structure III:

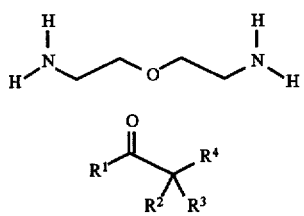

where

R¹ is hydrogen, a linear or branched C1–C4 alkyl, or a C1–C4 hydroxyalkyl group;

R² and R³ are independently hydrogen, hydroxy, a linear or branched C1–C4 alkyl, a linear or branched C1–C4 hydroxyalkyl group; and R⁴ is a linear or branched C1–C10 hydroxyalkyl group.

Reaction of compounds II and III afford hydroxyalkyl-bisaminoethyl ether IV which is permethylated to yield compound I

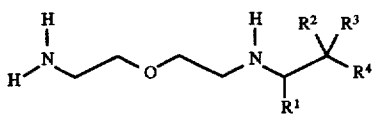

Exemplary of suitable structures for carbonyl compound III are hydroxybutyraldehyde, hydroxypropionaldehyde, glyceraldehyde, aldol (acetaldehyde dimer), acetol, 1-hydroxy-2-butanone and 3-hydroxy-2-butanone.

Another preferred route to catalyst compositions of structure I would be the methylation of bisaminoethyl ether II with a slight substoichiometric amount of formaldehyde and hydrogen to afford a bisaminoethyl ether V in combination with other methylated products. Bisaminoethyl ether V would then undergo reductive amination with carbonyl compound III to afford catalyst composition I.

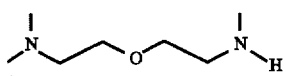

Alternatively, catalyst compositions of this type can be prepared from dimethylaminoethoxyethanol in a two step procedure. Step one is the amination of dimethylaminoethoxyethanol with methylamine to afford the bisaminoethyl ether V. Step two is the reductive amination of bisaminoethyl ether V with carbonyl compound III to afford I.

A catalytically effective amount of the catalyst composition is used in the polyurethane formulation. More specifically, suitable amounts of the catalyst composition may range from about 0.01 to 10 parts per 100 parts polyol (phpp), preferably 0.1 to 0.5 phpp, in the polyurethane formulation.

Catalyst compositions used in making polyurethanes may contain other tertiary amine, organotin and carboxylate urethane catalysts well known in the urethane art.

EXAMPLE 1

N,N,N'-Trimethylbis(aminoethyl) Ether (TMAEE)

A 1½ gallon stainless steel autoclave was charged with dimethylaminoethoxyethanol (DMAEE) and reduced/stabilized Cu/ZnO/Al₂O₃ catalyst From a sample cylinder connected to a port in the reactor head monomethylamine (MMA) was charged using a 6.5 bar $N_2$ head to assist in the transfer. After resealing the reactor and pressurizing it to 16 bar with $H_2$, the reactor was heated to the reaction temperature of 195°–205° C. and kept at that temperature for 24–25 hr. The reactor was then cooled to 25° C. and the reaction product was recovered after filtration to remove the catalyst particles. Table 1 shows the results from 2 reactions conducted using the above procedure.

TABLE 1

|  | Run 1 | Run 2 |
|---|---|---|
| Reactor charge (g): |  |  |
| DMAEE | 2200 | 2007 |
| MMA | 785 | 778 |
| Cu/ZnO/Al₂O₃ catalyst | 167.1 | 167.0 |
| Reaction Temp. (°C.): | 195 | 205 |
| Reaction time (hr): | 25 | 24 |
| Product Recovery (g): | 2924 | 2867 |
| Product Composition (wt %): |  |  |
| TMAEE | 20.9 | 32.6 |
| DMAEE | 39.2 | 35.5 |
| MMA | 10.6 | 12.4 |
| H₂O | 4.8 | 7.0 |
| other amines | 24.5 | 12.5 |

Reaction products from the above 2 runs were combined (370 g of product from run 1 and 321 g of product from run 2) and were heated under vacuum to remove the low boiling components, including H₂O and MMA. The remaining product was then distilled, under vacuum, through a 25 cm packed column. The overhead product (122.9 g) contained 103.6 g of TMAEE. This overhead product was used in the preparation of N,N,N'-Trimethyl-(4-hydroxybutyl)bis(aminoethyl)ether in Example 2 below.

EXAMPLE 2

N,N,N'-Trimethyl-(4-hydroxybutyl)bis(aminoethyl)ether

A 1-liter stainless steel autoclave reactor was charged with the overhead product from Example 1 (0.71 moles of N,N,N'-trimethylbis(aminoethyl)ether (TMAEE)) and 15.0 g of (52 wt % water-wet) 5% Pd on carbon catalyst. After purging the reactor with N₂ and H₂, the reactor was heated to 90° C. under a 400–500 psig H₂ blanket. Once at 90° C. the reactor pressure was raised to 800 psig with H₂. Then, a solution of hydroxybutyraldehyde containing 11.7% of 4-hydroxybutyraldehyde and 1.4% 3-hydroxy-2-methyl propionaldehyde in water, was fed via a syringe pump into the reactor at 100 ml/hr. over a 5 hour period. After feeding 500 ml of the above solution, the reaction mass was maintained at 90° C. for 15.5 hours. The reactor was then cooled to 25° C. and 585.2 g of reaction product was recovered after filtration to remove the catalyst particles. Gas chromatographic analysis showed that 100% of the TMAEE was converted and the reaction product contained 90.7 g (0.416 moles) of N,N,N'-trimethyl-(4-hydroxybutyl)bis(aminoethyl)ether and 8.54 g (0.039 moles) of the N,N,N'-trimethyl-(3-hydroxy-2-methylpropyl)bis(aminoethyl)ether isomer.

The reaction product was heated under vacuum in a rotary evaporator to remove water and any low boiling components. A short path distillation was then done at less than 1 mm Hg on 71.5 g of the reaction product to remove any heavies and leftover 5% Pd on carbon catalyst. GC analysis revealed that the overhead distillate (50.7 g), collected from 111° C. to 116° C. contained 45.05 g (0.207 moles) of N,N,N'-trimethyl-(4-hydroxybutyl)bis(aminoethyl)ether and 3.41 g (0.016 moles) of N,N,N'-trimethyl-(3-hydroxy-2-methylpropyl)bis(aminoethyl)ether. The overhead distillate was used in Example 3.

EXAMPLE 3

This example shows the catalysis of polyurethane foam with N,N,N'-trimethyl-(4-hydroxybutyl)bis(aminoethyl) ether. The foam reactivity of N,N,N'-trimethyl-(4-hydroxybutyl)bis(aminoethyl)ether was measured using triethylenediamine (TEDA) as the gelling catalyst and compared to the industrial standard blowing catalyst, BL-11 (a 70 wt % solution of bis(dimethylaminoethyl) ether in dipropylene glycol). In addition, a foam made with TEDA as the sole catalyst is provided as an example to show the effect of having no blowing co-catalyst. Table 2 sets forth conditions and results. TEDA was provided by DABCO 33-LV® catalyst, a 33% TEDA in dipropylenegylcol.

Times cited were from mixing of the polyol masterbatch with isocyanate. TOC 1 (top-of-cup 1) represents the time required for the foam formulation to fill a 16 oz (473 mL) cup and is an indication of reaction initiation. TOC 2 (top-of-cup 2) represents the time required for the foam formulation to fill a 1 gal (3.8 L) cup in addition to the 16 oz (473 mL) cup mentioned above and is an indication of reaction progression. String Gel and Full Rise are further measures of reaction progression and provide some indication of extent of cure.

These results indicate that N,N,N'-trimethyl(4-hydroxybutyl)bis(aminoethyl)ether does make a polyurethane foam and acts also as a polyurethane blowing catalyst.

TABLE 2

| Catalyst | Blowing catalyst (mmol) | TOC 1 (sec) | TOC 2 (sec) | Gel (sec) | Full Rise (sec) | Height (mm) | Final Height (mm) |
|---|---|---|---|---|---|---|---|
| Cat. A | 1.27 | 8.83 | 27.95 | 49.47 | 82.70 | 427.35 | 390.43 |
| Cat B |  | 13.65 | 39.84 | 67.49 | 111.25 | 419.35 | 397.79 |
| Cat. C | 1.56 | 9.61 | 27.88 | 54.97 | 90.65 | 429.44 | 388.64 |

Cat. A: 0.5 pphp DABCO 33-LV and 0.15 pphp BL-11
Cat. B: 0.5 pphp DABCO 33-LV
Cat. C: 0.5 pphp DABCO 33-LV and 0.18 pphp N,N,N'-trimethyl-(4-hydroxybutyl)-bis(aminoethyl)ether

STATEMENT OF INDUSTRIAL APPLICATION

The catalysts of the present invention are useful in the production of polyurethane foams.

We claim:

1. A method for preparing a polyurethane foam which comprises reacting an organic polyisocyanate and a polyol in the presence of a blowing agent, a cell stabilizer and a catalyst composition comprising N,N,N'-trimethyl-N'-(2,3-dihydroxypropyl)bis(aminoethyl) ether.

2. In a method for catalyzing the reaction between an isocyanate and a compound containing a reactive hydrogen, improvement which comprises using a catalyst composition comprising N,N,N'-trimethyl-N'-(2,3-dihydroxypropyl)bis(aminoethyl) ether.

* * * * *